(12) United States Patent
Arai et al.

(10) Patent No.: US 6,610,913 B1
(45) Date of Patent: Aug. 26, 2003

(54) RICE PLANTS TRANSFORMED TO PROVIDE A PCK-TYPE C4 CYCLE AND METHODS OF MAKING

(75) Inventors: Masao Arai, Shizuoka-ken (JP); Shoichi Suzuki, Shizuoka-ken (JP); Nobuhiko Murai, Shizuoka-ken (JP); Shigehiro Yamada, Shizuoka-ken (JP); Shozo Ohta, Shizuoka-ken (JP); James N. Burnell, Qeensland (AU)

(73) Assignee: Japan Tobacco, Inc., Tokyo (JP)

( * ) Notice: Subject to any disclaimer, the term of this patent is extended or adjusted under 35 U.S.C. 154(b) by 0 days.

(21) Appl. No.: 09/155,989

(22) PCT Filed: Feb. 10, 1998

(86) PCT No.: PCT/JP98/00537
§ 371 (c)(1),
(2), (4) Date: Dec. 10, 1998

(87) PCT Pub. No.: WO98/35030
PCT Pub. Date: Aug. 13, 1998

(30) Foreign Application Priority Data

Feb. 10, 1997  (JP) .............................................. 9-026658

(51) Int. Cl.[7] ........................ C12N 15/29; C12N 15/82; C12N 15/54; C12N 9/12; A01H 5/00

(52) U.S. Cl. ............................. 800/320.2; 435/320.1; 435/419; 435/468; 435/194; 435/69.8; 536/23.6; 800/278; 800/284; 800/287; 800/298

(58) Field of Search ............................. 435/320.1, 69.8, 435/468, 419, 194; 800/278, 284, 287, 298, 320.2; 536/23.6

(56) References Cited

U.S. PATENT DOCUMENTS

| | | | |
|---|---|---|---|
| 4,757,009 A | 7/1988 | Sano et al. | 435/106 |
| 4,970,160 A | 11/1990 | Katsuki | 435/232 |
| 5,591,616 A | 1/1997 | Hiei et al. | 435/469 |

FOREIGN PATENT DOCUMENTS

| | | |
|---|---|---|
| AU | 28989/95 | 2/1996 |
| EP | 0190362 B1 | 8/1986 |
| EP | 0672752 A1 | 9/1995 |
| EP | 0682117 A1 | 11/1995 |
| EP | 0690128 A1 | 1/1996 |
| JP | 4222527 A | 8/1992 |
| JP | 6090766 A | 4/1994 |
| JP | 6319567 A | 11/1994 |
| JP | 7184657 A | 7/1995 |
| WO | 96 01895 | 1/1996 |

OTHER PUBLICATIONS

Makoto Matsuoka, The Gene of Pyruvate, Orthophosphate Dikinase in C4 Plants: Structure, Regulation and Evolution, 1995, Plant Cell Physiology, vol. 36, No. 6, pp. 937–943.*

Ishimaru et al, Analysis of a C4 Maize Pyruvate, Orthophosphate Dikinase Expressed in C3 Transgenic Arabidopsis Plants, 1997, Plant Science, Vo. 129, pp. 57–64.*

Jae Kim et al, Molecular Cloning of Cucumber Phosphoenolpyruvate Carboxykinase and Developmental Regulation of Gene Expression, 1994, Plant Molecular Biology, vol. 26, pp. 4230434.*

Salisbury et al, Plant Physiology, Second Edition, 1978, Chapter 10, p. 144.*

Plant Physiol. (1992) vol. 98, pp. 458–464, Hudspeth et al.

Transgenic Research. (1994) vol. 3, pp. 287–298, Hiroyuki Kogami et al.

American Journal of Botany (1996) vol. 83, No. 11, pp. 1458–1470, Neelima R. Sinha et al.

Hudspeth et al., *Plant Physiol.*, vol. 98, pp. 458–464 (1992).

Kogami et al., *Transgenic Research*, vol. 3, pp. 287–296 (1994).

Majeau et al., *Plant Molecular Biology*, vol. 25, pp. 377–385 (1994).

Gustine et al., *Plant Physiol.*, vol. 110, pp. 713–714 (1996).

Koizumi et al., *Plant Molecular Biology*, vol. 17, pp. 535–539 (1991).

Merkelbach et al., *Plant Molecular Biology*, vol. 23, pp. 881–888 (1993).

Pathirana et al., *Plant Molecular Biology*, vol. 20, pp. 437–450 (1992).

Cushman et al., *Nucleic Acids Research*, vol. 17, No. 16, pp. 6743–6744 (1989).

Kim et al., *Plant Molecular Biology*, vol. 26, pp. 423–434 (1994).

Medina et al., *Journal of Bacteriology*, vol. 172, No. 12, pp. 7151–7156 (Dec. 1990).

Østerås et al., *Journal of Bacteriology*, vol. 177, No. 6, pp. 1452–1460 (Mar. 1995).

Keegstra et al., *Annu. Rev. Plant Physiol. Plant Mol. Biol.*, vol. 40, pp. 471–501 (1989).

Sültemeyer et al., *Physiologia Plantarum*, vol. 88, pp. 179–190 (1993).

Raines et al., *Plant Molecular Biology*, vol. 20, pp. 1143–1148 (1992).

(List continued on next page.)

*Primary Examiner*—David T. Fox
*Assistant Examiner*—David H. Kruse
(74) *Attorney, Agent, or Firm*—Birch, Stewart, Kolasch & Birch, LLP (57) ABSTRACT

The present invention relates a method for transforming a rice plant to provide it with a C4 photosynthetic pathway by way of the introduction of some genes participating in a C4 photosynthetic pathway. To this end, the method of the invention comprises introducing a phosphoenolpyruvate carboxylase (PEPC) and a gene coding for a phosphoenolpyruvate carboxykinase (PCK) which has been connected with a DNA fragment coding for a transit peptide into a rice plant.

12 Claims, 4 Drawing Sheets

OTHER PUBLICATIONS

Matsuoka et al., *The Journal of Biological Chemistry*, vol. 263, No. 23, pp. 11080–11083 (1988).

Rosche et al., *Plant Molecular Biology*, vol. 26, pp. 763–769 (1994).

Fisslthaler et al., *Planta*, vol. 196, pp. 492–500 (1995).

Glackin et al., *Proc. Natl. Acad. Sci. USA*, vol. 87, pp. 3004–3008 (Apr. 1990).

Hudspeth et al., *Plant Molecular Biology*, vol. 12, pp. 579–589 (1989).

Kyozuka et al., *Plant Physiol.*, vol. 102, pp. 991–1000 (1993).

Sakamoto et al., *Plant Cell Physiol*, vol. 32(3), pp. 385–393 (1991).

Gehlen et al., *Plant Molecular Biology*, vol. 32, pp. 831–848 (1996).

Ishimaru et al., *Physiologia Plantarum*, vol. 103, pp. 340–346 (1998).

Burnell et al., *Plant Physiol.*, vol. 92, pp. 37–40 (1990).

Poetsch et al., *FEBS Letters*, vol. 292, No. 1.2, pp. 133–136 (Nov. 1991).

Roeske et al., *Nucleic Acids Research*, vol. 18, No. 11, pp. 3413–3414 (1990).

Suzuki et al., *Plant Cell Physiol.*, vol. 39, Supplement, p. s23 (1998).

N. Murai et al., *Proceedings of the $91^{st}$ Meeting of Jap. Soc. Plant Breeding*, p. 167 (1997).

Proceedings of the CropScience Society of Japan (1994) vol 63, separate vol., No. 2, pp. 247–248 Hiroaki Ichikawa et al., figures only.

\* cited by examiner

GENE CONSTRUCT USED IN THE TRANSFORMATION

GENE CONSTRACT FOR THE INTRODUCTION OF TWO GENES

GENE CONSTRACT FOR THE INTRODUCTION OF THREE GENES

GENE CONSTRACT FOR THE INTRODUCTION OF FOUR GENES

➡ PROMOTER

▭ cDNA

◄ TERMINATOR

▫ TRANSIT PEPTIDE REGION OF RICE RUBISCO SMALL SUBUNIT

▫ FIRST INTRON OF CASTOR BEAN CATALASE

Fig. 3 BEHAVIOR OF LABELED CARBON COMPOUNDS WITH THE PASSAGE OF TIME

—●— CALVIN CYCLE INTERMEDIATE
—■— PHOTORESPIRATION INTERMEDIATE
—▲— SUCROSE
—○— $C_4$ COMPOUND

CALVIN CYCLE INTERMEDIATE:
  3PGA + SUGAR PHOSHATE
PHOTORESPIRATION INTERMEDIATE:
  SERINE + GLYCINE + GLYCOLATE
C4 COMPOUND :
  MALATE + ASPARTATE

Fig. 4

PHOTOSYNTHETIC ACTIVITY OF CONTROL RICE (TSUKINOHIKARI) AND TRANSFORMANT RICE HAVING THREE INTRODUCED GENES (PHOTOSYNTHETIC ACTIVITY – INTERCELLULAR $CO_2$ CONCENTRATION CURVE)

RICE PLANTS TRANSFORMED TO PROVIDE A PCK-TYPE C4 CYCLE AND METHODS OF MAKING

This application is the national phase under 35 U.S.C. §371 of prior PCT International Application No. PCT/JP98/00537 which has an International filing date of Feb. 10, 1998 which designated the United States of America, the entire contents of which are hereby incorporated by reference.

BACKGROUND OF THE INVENTION

The present invention relates to a process for transforming a C3 plant to provide it with a C4 cycle by introducing two or more enzymes which participate in the C4 photosynthetic pathway.

PRIOR ART

Three types of photosynthetic pathway are known in higher plants, namely, C3, C4 and CAM types. Leaf tissues of plants having a C4 type photosynthetic pathway (hereafter sometimes referred to as C4 plants) comprise mesophyll cells and bundle sheath cells existing around fibro vascular bundles, forming the specific leaf tissue structure called Kranz-type anatomy. C4 plants fix carbon dioxide into a C4 compound by the action of a phosphoenolpyruvate carboxylase (hereafter sometimes referred to as PEPC) located in the cytoplasm of mesophyll cells. The fixed carbon dioxide is released by decarboxylase in bundle sheath cells, which increases the level of carbon dioxide in the vicinity of ribulose-1,5-biphosphate carboxylase/oxygenase (hereafter sometimes referred to as Rubisco) which is the enzyme for the essential carbon dioxide fixation. The metabolite resulting from the decarboxylation in the bundle sheath cells is transferred into mesophyll cells and converted to phosphoenolpyruvate (hereafter sometimes referred to as PEP), a substrate for PEPC, by the action of the pyruvate, orthophosphate dikinase (hereafter sometimes referred to as PPDK) located in mesophyll cells, with a simultaneous consumption of ATP. Namely, the two types of cells in green leaves of C4 plants are functionally differentiated; mesophyll cell is the place of formation of the C4 compounds at the initial carbon fixation as well as the place of re-generation of the PEPC substrate, while the bundle sheath cell is the place of decarboxylation of the C4 compound and essential carbon dioxide fixation by way of the Calvin-Benson cycle.

The three steps i.e., the carbon dioxide fixation by PEPC, the release of carbon dioxide in the vicinity of Rubisco, and the re-generation of PEPC substrate accompanied by the consumption of ATP, constitute a system of cycle reaction which is called a C4 photosynthetic pathway. The pathway provides C4 plants with an enhanced ability to accumulate carbon dioxide, and to avoid the decrease of photosynthetic efficiency which may otherwise take place under high light intensity due to the over production of ATP (avoidance of photoinhibition). These properties are not found in C3 plants having a regular photosynthetic pathway (C3 type photosynthesis). Thus, C4 plants do not exhibit photorespiration as in C3 plants, and therefore, the former shows less deterioration in the efficiency of photo-synthesis than the latter when placed under an atmosphere which is dried, highlight intensity or high temperature. As such, C4 plants are superior to C3 plants in their ability to conduct photo-synthesis.

One might expect that a C4 photosynthetic pathway could be introduced in a C3 plant by means of crossing and breeding. However, most species having a C4 photosynthetic pathway and those having a regular C3 photosynthetic pathway are grouped into different genus or family, and crossing between them is difficult. Moreover, an attempt to introduce properties of a C4 plant wherein a C3 plant was crossed with a C4 plant selected from the same genus orache did not succeed (Ohsugi, R. Nogyo-gijutsu (1995) Vol.50, pp.30–36).

Hudspeth, et al. observed that the green leaves of transgenic tobacco into which PEPC gene was introduced under the control of tobacco chlorophyll a/b binding protein gene promoter (cab promoter) showed the doubling or PEPC activity and the increase of malate level (Hudspeth, et al., Plant Physiol., (1992) 98: 458–464). Kogami, et al. observed that the green leaves of transgenic tobacco into which PEPC gene was introduced under the control of cauliflower mosaic virus 35S promoter contained about twice as much PEPC activity as non-transformed toabcco (Kogami, et al., Transgenic Research (1994) Vol.3: 287–296).

Thus, Hudspeth, et al. and Kogami, et al. simply observed the accumulation of the C4 compound malate without confirming any change in photosynthetic property caused by the introduction of PEPC as a single gene into the C3 plant tobacco. The cells of C3 plants are incapable of rapidly decarboxylating a C4 compound to supply the carbon dioxide to the Calvin cycle. Therefore, it would not be possible, by way of a simple introduction of PEPC gene into a C3 plant, in an attempt to provide the plant with the capability of C4 photosynthetic pathway to concentrate carbonate or avoid a photoinhibition, when an improvement in the photosynthetic property of a C3 plant is desired.

Japanese Patent Public Disclosure Hei 8-80197 discloses that a DNA fragment encoding transit peptide was connected with a phosphoenolpyruvate carboxykinase (PCK) gene. The chimeric gene was introduced into rice, which is a C3 plant, whereby the enzyme activity in the crude extract of green leaves was detected as well as the localization of PCK protein in chloroplasts. These facts indicate that it is possible to allow the activity of PCK to localize in chloroplasts. However, no description is made about the establishment of a C4 photosynthetic pathway or change of photosynthetic property in the transgenic plants.

Ichikawa, et al., Nihon Sakumotsu Gakkai Kiji, Vol.63, Suppl.2, (1994), p.247) disclose that when PPDK was introduced into C3 plants, Arabidopsis and tomato, the protein was accumulated in the plants. However, no description is made about the establishment of a C4 photosynthetic pathway or change in the photosynthetic property of the transgenic plants. Japanese Patent Publication Hei 6-12990 discloses the change in the photosynthetic efficiency in the cotyledonous protoplasts of *Lycopersicon esculentum* wherein carbonic anhydrase (herein under sometimes referred to as CA) protein was incorporated. On the other hand, Majeau et al., disclose that the in vivo over expression of CA did not give rise to any change in the photosynthetic ability of the plant (Plant Mol. Biol. (1994) 25: 337–385).

As discussed above, previous attempts to introduce a gene from a C4 photosynthetic pathway into a C3 plant by a genetic engineering method were limited to the introduction of CA, PEPC, PCK or PPDK gene as a single gene. These attempts failed to confirm any C4 photosynthetic pathway or change in the efficiency of photosynthesis, even if the expression of the introduced gene or the enzyme activity was observed in some attempts.

SUMMARY OF THE INVENTION

An object of the present invention is to provide a method for improving the photosynthetic property of C3 plants.

Specifically, the present invention provides a method for transforming a C3 plant to provide it with a C4 photosynthetic pathway by means of the introduction of two or more enzymes which take part in C4 photosynthetic pathway.

Another object of the present invention is to provide a plant which has been transformed to have a C4 pathway in accordance with the method of the invention.

A further object of the present invention is to provide a vector which is useful for conducting the transformation of a C3 plant.

DETAILED EXPLANATION

The present invention has been accomplished as a result of extensive study by the inventors by introducing PEPC gene into a C3 plant together with PCK gene which has been connected with the DNA fragment coding for a transit peptide.

The present inventors focused on the fact that in previous attempts the respective gene of C4 photosynthetic components was introduced into cytoplasm of a C3 plant as a single gene. Thus, the inventors assumed that the above fact may account for the reason why previous attempts failed to actuate the C4 photosynthetic pathway or improve the photosynthetic property even though some of the transgenic C3 plants acquired the activity of the introduced enzymes.

On the basis of said assumption, the present inventors have designed a system wherein: the genes of two or more enzymes are introduced in a C3 plant in such a manner that each enzyme will be expressed at a defined intracellular localization; chloroplasts will undertake the role of bundle sheath cells of a C4 plant; and said two or more enzymes required in the C4 photosynthetic pathway will be expressed simultaneously in green mesophyll cells. In accordance with said design, it is possible not only to provide a C3 plant with respective enzyme activity, but also to enable the C3 plant to utilize a cycle reaction which mimics the C4 photosynthetic pathway of C4 plants, thereby to enhance the ability to accumulate carbon dioxide in chloroplasts and avoid photoinhibition which may be caused by an excessive consumption of ATP. It is expected that plants provided with such properties will exhibit improved productivity, improved tolerance to drought, improved tolerance to high temperature and an improved photosynthetic property under low carbon dioxide conditions, as a result of the improvement of photosynthetic property.

The method of the present invention for providing the C4 photosynthetic pathway comprises: providing mesophyll cells of a green leaf of C3 plant (e.g. rice); allowing the enzyme (PEPC) of the first carbon dioxide fixation process of a C4 plant to act in the cytoplasm of said cells; allowing a decarboxylase for the C4 compound to act in chloroplasts of said cells; and simultaneously allowing the expression of an enzyme to regenerate PEP either in the cytoplasm or chloroplasts of said cells.

Decarboxylases useful for said purpose include PCK. PCK is the enzyme which decarboxylates oxaloacetate to generate PEP while it consumes ATP. Thus, PCK can be advantageously used as a decarboxylase since decarboxylation, consumption of ATP, and re-generation of PEP can be effected by the single enzyme. In order to enable a decarboxylase to exhibit its activity in chloroplasts, the gene for this enzyme is connected with a sequence of transit peptide. The transit peptide conveys the decarboxylase polypeptide into chloroplasts to allow the enzyme to exhibit its function in the chloroplasts.

Figure 1:
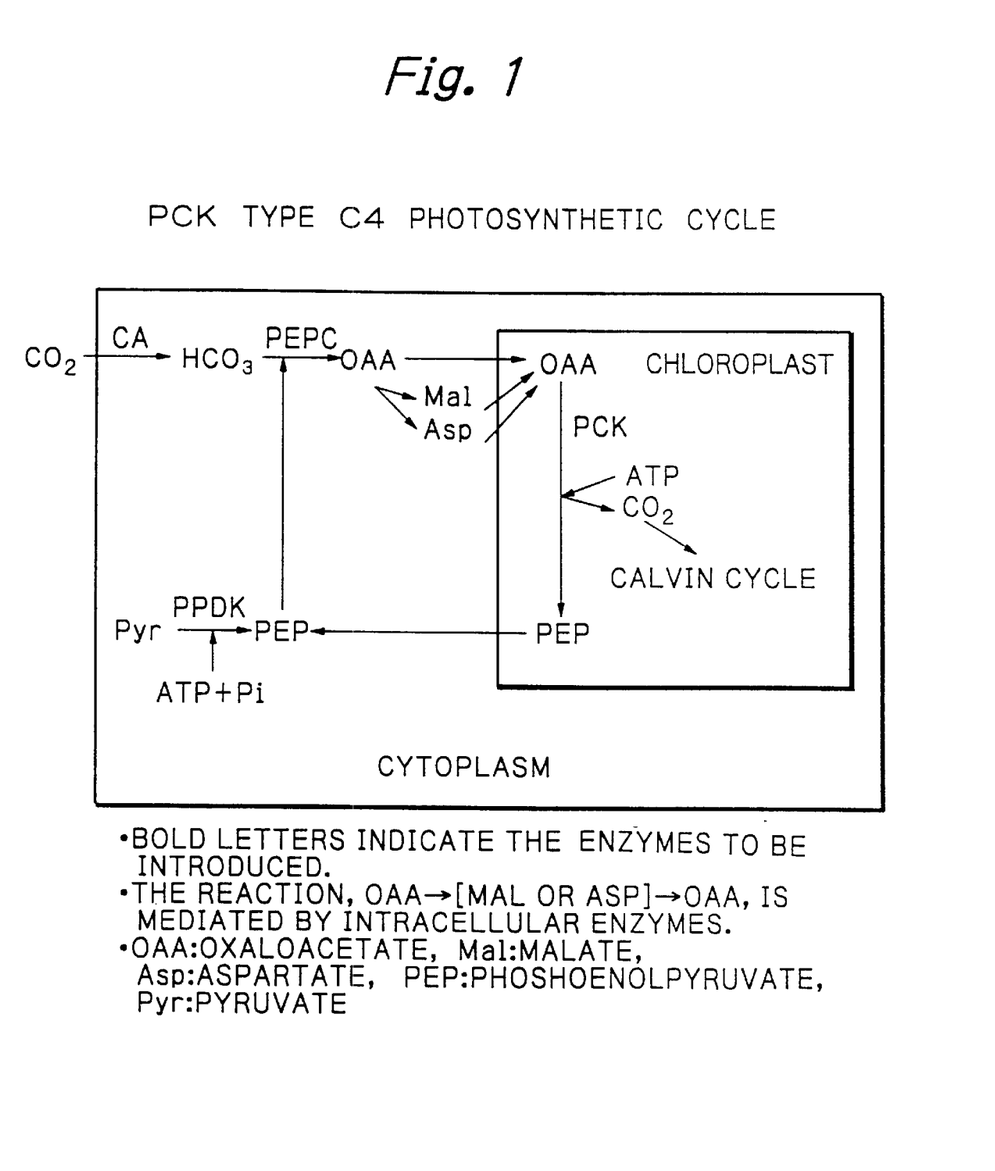
FIG. 1 is an illustration of the PCK type C4 photosynthesis cycle.

By means of the transformation as stated above, the carbon dioxide fixation pathway which mimics the C4 photosynthetic pathway derived from the differentiated leaf tissue structure of C4 plants is constituted in a C3 plant, wherein the cytoplasm of the C3 plant green leaf mesophyll cells mimic mesophyll cells of C4 plants, and the chloroplasts of C3 plants mimic the bundle sheath cells of C4 plants (FIG. 1). Thus, it is possible to provide a C3 plant with an ability to concentrate carbon dioxide and avoid photoinhibition.

The combination of PEPC, decarboxylase and an enzyme for re-generating PEP will be sufficient to constitute the desired C4 photosynthetic pathway. However, in a preferred embodiment, CA may be co-expressed in cytoplasm to supply bicarbonate ion as the direct substrate of PEPC so that the C4 photosynthetic pathway will function more smoothly. Further, PPDK which catalyses the formation of PEP from pyruvate may be co-expressed in addition to PEPC, PCK and CA, if an increased supply of PEP as the substrate for PEPC is desired, whereby the C4 photosynthesis cycle will function still more smoothly.

The present invention will be described in greater detail in the following.

The present invention relates to a method for transforming a C3 plant to provide it with a C4 photosynthetic pathway by way of introducing into said plant a gene coding for PEPC, a gene coding for PCK which has been connected with a DNA fragment coding for a transit peptide.

PEPC genes which may be used in the present invention include PEPC genes from bacteria, protozoas, plants, and so on. As a specific example of bacterial PEPC gene, that of a glutamate producing strain of Corynebacterium is known (Japanese Patent Publication Hei 7-83714).

However, preferred PEPCs are of plant origin, for example those derived from maize (Japanese Patent Publication Hei 6-30587), Amaranthus (Rydzik, E. and Berry, J. O., Plant Physiol., (1995) 110:713), *Flaveria trinervia* (Poetsch, W., et al., FEBS Lett., (1991) 292:133–136), tobacco (Koizumi, N., et al., Plant Mol. Biol., (1991) 17:535–539), soybean (Japanese Patent Public Disclosure Hei 6-319567), rape (Japanese Patent Public Disclosure Hei 6-90766), potato (Merkelbach, S., et al., Plant Mol. Biol., (1993) 23:881–888), alfalfa (Pathariana, S. M., et al., Plant Mol. Biol., (1992) 20:437–450), *Mesembryanthenum crystallinum* (Cushman, J. C. and Bohnart, H. J., Nuc.Acid Res., (1989 6743–6744) are preferred. PEPC of maize is especially preferred.

Examples of PCK encoding genes used in the present invention are ATP dependent ones derived from plants and bacteria. Examples of plant PCK include those from *Urochloa panicoides* (Japanese Patent PublicDisclosure Hei 8-80197) and cucumber (Kim, D.-J. and Smith, S. M., Plant Mol. Biol., (1994) 26: 423–434), and examples of bacterial PCK include those from *E. coli* (Medina, V. et al.,J. Bacteriol., (1990) 172: 7151–7156) and Rhizobium (Osteras, M. et al., J. Bacteriol., (1995) 177: 1452–1460). PCK gene derived from a plant, especially from *Urochloa panicoides*, is preferred.

Further, it is required that PCK exhibits its function in chloroplasts, as described above. In order to ensure this, a DNA fragment encoding transit peptide sequence is connected with the PCK gene.

A number of transit peptide sequences which may be connected with PCK gene have been reported in proteins localized in chloroplasts (Keegstra, K. et al., Annu. Rev. Plant Mol. Biol., (1989) 40: 471–501). It is preferred in the present invention that the transit peptide sequence is derived from rice proteins. Especially preferred, transit peptide sequence is the sequence of Rubisco small subunit (SEQ ID NO:2) which can be obtained according to the method shown in examples hereinafter. The DNA fragment encoding a transit peptide sequence is connected in frame with PCK structural gene at an upstream, and preferably the immediate upstream thereof.

In the present invention, a gene encoding CA may further be introduced to C3 plants into cytoplasm for providing hydrogencarbonate ion as the substrate for PEPC as described above.

A number of genes encoding CA which may be used in the present invention are known such as those derived from animals and plants. However, sequence homologies between CAs of higher plants and other organisms are not high. Further, the enzyme activity of CA from higher plants is affected by inorganic phosphate (Sultemeyer, D. et al., Physiol. Plant., (1993) 88: 179–190). Therefore, it is preferred that the gene is derived from a plant, such as spinach (Burnell et al., Plant Physiol., (1990) 92: 37–40), pea (Roeske, C. A. and Ogren, W. L., Nuc. Acid Res., (1990) 18: 3413), Arabidopsis (Raines, C. A. et al., Plant Mol. Biol., (1992) 20: 1143–1148), rice (WO95/11979) and maize (WO95/11979). Especially preferred is the CA derived from spinach. Because spinach CA is localized in chloroplasts, the gene of the enzyme contains a transit peptide encoding region. Thus, SEQ ID NO:4, the transit peptide encoding region is eliminated by the induction of a point mutation as described in Example 1 and the gene having the sequence represented by SEQ ID NO:4, is used for the genetic construction.

Genes encoding PPDK used in the present invention include maize C4 type PPDK gene (Matsuoka, M. et al., J. Biol. Chem., (1988) 263: 11080–11083), rice PPDK gene (Japanese Patent Public Disclosure Hei 7-184657), *Flaveria pringlei* PPDK gene (Rosche, E. et al., Plant Mol. Biol., (1994) 26: 763–769), *Mesembryanthemum crystallinum* (Fisslthaler, B. et al., Planta, (1995) 196: 492–500), and maize C4 type PPDK gene is preferred.

PPDK gene may be expressed either in chloroplasts or in cytoplasm. If it is desired to express PPDK gene in chloroplasts, the gene may have been connected with a DNA fragment coding for transit peptide.

Promoter sequences useful for expressing the gene of the above enzymes, not to be limited to any specific ones, although those which are specific to a photosynthetic organ are preferred. For example, maize C4 type PPDK promoter (Glackin et al., (1990) Proc. Natl. Acad. Sci. USA, 87: 3004–3008), maize C4 type PEPC promoter (Hudspeth, R. L. and Grula, J. W., Plant Mol. Biol., (1989) 12: 579–589), rice Rubisco small subunit promoter (Kyozuka, J. et al., Plant Physiol., (1993) 102: 991–1000), and light-harvesting chlorophyll a/b binding protein promoter (Sakamoto, M. et al., Plant Cell Physiol., (1991) 32: 385–393) are preferred. Maize C4 type PPDK promoter is especially preferred. In the Examples hereinafter, SEQ ID NO:1 is used as the promoter.

In accordance with the present invention, the gene which encodes each of the above mentioned enzymes of C4 pathway may be carried on a separate gene construct (gene-introducing construct) which is used to transform a C3 plant. However, preferably, two or more of the genes are carried on a single gene-introducing construct which is introduced into a C3 plant to effect a transformation thereof. In that case, there is no specific limitation with regard to the order of genes.

Transformation of C3 plant cells with such a gene-introducing construct comprising derived genes independently or linked together may be conducted according to a standard method by introducing the gene-introducing construct into the cells of a selected C3 plant. General methods for gene introduction are known in the art such as electroporation, electroinjection, chemical treatment with, e.g., polyethylene glycol (PEG) and genetic bombardment. Among them, it is preferred that the genes are introduced to transform C3 plant cells using the Agrobacterium method. The Agrobacterium method is well known in the art and capable of transforming both dicotyledons (e.g. Japanese Patent Public Disclosure Hei 4-330234) and monocotyledons (WO94/00977). Successful transformants can be selected by the method described hereinafter.

Phenotypes of transformants can be fixed by any appropriate conventional breeding methods and, hence, an introduced gene can be transferred to the progeny of the transformants.

The method of the present invention can be applied to any C3 plants, and the method is especially beneficial for crops such as rice, wheat, barley, soybean, potato, tobacco, rape and the like, whereas productivity per dry weights is expected to be raised due to the increase of photosynthetic ability. Preferably, the invention is applied to monocotyledons, most preferably to rice.

The C4 photosynthetic pathway in the present invention is constituted by the three processes, that is, the carbon dioxide fixation by PEPC described above, the release of carbon dioxide in the vicinity of Rubisco by decarboxylase and the regeneration of substrates for PEPC using ATP.

The method to confirm that the C4 photosynthetic pathway functions in a transformed C3 plant will be described in detail in Examples hereinafter. Briefly, the method comprises:

(1) studying whether a C4 compound as the initial product is formed by the action of PEPC in the transformants when detached leaves of the transformant and control plants are allowed to incorporate radioactive carbon dioxide ($^{14}CO_2$) or studying whether the introduced C4 photosynthetic pathway functions in the transformant by chasing the proportion of labeled carbon compounds with the passage of time;

(2) studying whether the decarboxylation of C4 compound functions by the action of PCK in the transformants when detached leaves of the transformant and control plants are allowed to incorporate radioactive malate ($[^{14}C]$ malate) and the relative amount of labeled sucrose after a determined time period is compared between the transformant and control plants; and/or (3) studying any changes in photosynthetic property in the transformant by measurement of photosynthetic property.

EXAMPLES

To further illustrate the present invention in greater detail, and not by way of limitation, the following Examples will be given. A. C4 photosynthetic pathway of PCK type

Example 1

Construction of Transgenes
(1) Promoter Sequence

The DNA fragment of the corn C4 type PPDK promoter region was obtained by the PCR method (Mcpherson, M. J., Quirke, P. and Taylor, G R. ed.: PCR. A practical approach, Oxford Express Press, Oxford N.Y. (1991)) with the use of the following two synthetic primers prepared on the basis of a known nucleotide sequence (Glackin, C. A. and Grula, J. W. (1990) Proc. Natl. Acad. Sci. USA 87:3004–3008):

5'-CTAAAGACATGGAGGTGGAAG-3' (5' side) (SEQ ID NO: 6)

5'-GTAGCTCGATGGGTGCACG-3' (3' side) (SEQ ID NO: 7).

The amplification was carried out by using maize genomic DNA as the template, which had been obtained by extracting total nucleic acids from a maize inbred B73 green leaf by the SDS-phenol method followed by purification by cesium chloride-ethidium bromide ultracentrifugation. The DNA fragment thus obtained was inserted into the cloning site of a plasmid vector pCR1000 (manufactured by Invitrogen, USA). The plasmid thus obtained was digested with SacI and blunt-ended, and then an NcoI linker was added thereto. After being digested with HindIII, the obtained 950 bp DNA fragment containing PPDK promoter region was used in the gene construction. SEQ ID NO: 1 shows the DNA sequence employed therein.

(2) PEPC Gene

The cDNA of maize C4 PEPC was isolated by screening 20,000 clones from a cDNA library obtained by using mRNA prepared by the guanidine-hydrochloric acid method from green leaves of maize seedlings (hybrid variety "harvest queen") and λZAP vector (manufactured by Stratagene, U.S.A.) in accordance with the instruction given in the attached manual with the use of the following synthetic oligonucleotide, as a probe, prepared based on a known nucleotide sequence (Hudspeth, R. L. and Grula, J. W. (1989) Plant Mol. Biol. 12: 579–589):

5'-GCCATGGCGCGGCGGGAAGCTAAGCACGG AAGCGA-3' (SEQ ID NO: 8)

by a conventional method (Sambrook, J., Fritsch, E. F. and Maniatis, T. ed.: Molecular Cloning: A Laboratory Manual, 2nd ed., Cold Spring Harbor Laboratory Press, Cold Spring Harbor N.Y. (1989)). The clone thus obtained was digested with Xho I and then partially digested with NcoI. The DNA fragment of about 3 kbp thus obtained was employed in the gene construction.

(3) PCK Gene

The cDNA of *Urochloa panicoides* PCK was used in a gene construct wherein the region encoding the transit peptide of rice Rubisco small subunit has been added as reported previously (Japanese Patent Public Disclosure Hei 8-80197). Namely, λPCK170204 and λPCK100101 were ligated together at the KpnI sites existing in the inserts thereof. By using the DNA fragment thus obtained as a template, PCR was carried out with the use of the following synthetic primers:

PCK-f2:
5'-GCTCTAGATCTCTGGCACGTGAATATGG CCCCAACCTCG-3' (SEQ ID NO:9); and

PCK-r2: 5'-CAGTGCATGCCGCCGAACAGGCATACA GATTTACACCAG-3' (SEQ ID NO:10).

Separately, a DNA fragment encoding the transit peptide of rice Rubisco small subunit was isolated by the PCR method with the use of the following primers synthesized based on the sequence of rice Rubisco small subunit (Matsuoka et al., Plant Cell Physiol. 29:1015–1022 (1988)):

TP-f1:
5'-GGAATTCCATGGTGCATCTCAAGAAGTAC-3' (SEQ ID NO:11); and

TP-r1: 5'-GCTCTAGACTGCATGCACCTGATCC-3' (SEQ ID NO: 12).

The template was a rice genomic DNA which had been prepared from green leaves of Japanese rice variety "Nihonbare" by the SDS-phenol method.

By using the amplified DNA fragment as a template, PCR was performed again by using the following synthetic primer:

TP-f2: 5'-GGAATTCCATGGCCCCCTCCGTGATGG-3' (SEQ ID NO: 13); and the above-mentioned primer TP-r1. Next, a DNA fragment of about 2 kbp obtained by partial digestion of the PCK cDNA fragment amplified by the PCR with XbaI and SphI was ligated with a fragment of about 150 bp (represented by SEQ ID NO: 2) obtained by digestion of the transit peptide sequence DNA fragment amplified by the second PCR with NcoI and XbaI. The resulting DNA fragment of about 2.2 kbp was employed in the gene construction.

(4) CA Gene

A vector was obtained by inserting a fragment of 1.8 kbp containing the spinach CA cDNA region (which are obtained by digesting a λ phage clone (λLCA48) reported previously (Burnell, J. N. et al. (1990) Plant, Physiol. 92:33–40) with HindIII and KpnI) into the HindIII/KpnI site of pBluescriptSK—(manufactured by Stratagene, U.S.A.). From this cDNA, the region encoding the transit peptide which participates in the transport of CA into chloroplasts was deleted. In order to effect the deletion, the final amino acid residue in the transit peptide region was altered from serine to methionine so that the point mutation would introduce an NcoI recognition site. The mutation was effected with the use of the following synthetic oligonucleotide:

5'-GGTGGCACAGATAACCATGGATCCAGTTAG CCGACGGTGGC-3' (SEQ ID NO: 14); and Mutan-K™ (manufactured by Takara Shuzo Co., Ltd.). The obtained plasmid carrying the mutation was digested with NcoI to thereby delete the region encoding the transit peptide therefrom. This plasmid was then digested with SphI and the obtained DNA fragment of about 700 bp was employed in the gene construction. SEQ ID NO: 4 shows the sequence of said fragment.

(5) Terminator Sequences

The terminator regions, used were a DNA fragment of the NOS terminator region obtained by digesting pBI121 (Jefferson, R. A. (1987) Plant Mol. Biol. Reptr. 5:387–405) with SalI and EcoRI, and a DNA fragment of the 35S terminator region obtained by digesting pGL2 (Bilang, R. et al. (1991) Gene 100:247–250) with SphI and EcoRI.

(6) Construction of Plasmids for Introduction

Figure 2:
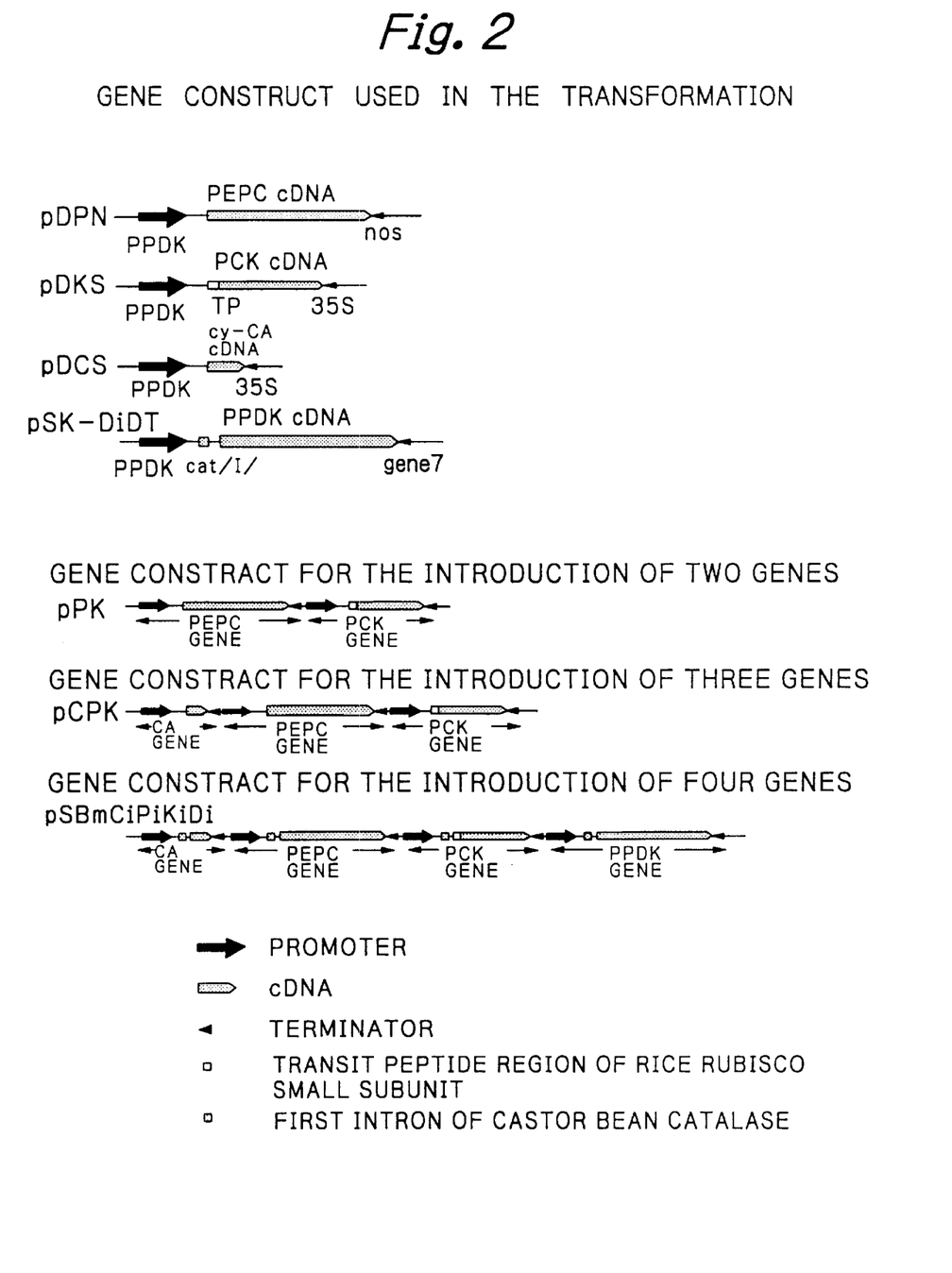
FIG. 2 is an illustration of the gene construct used in the transformation of a C3 plant.

The promoter, cDNA and terminator DNA fragments thus obtained were combined and ligated as indicated below and then inserted between the HindIII-EcoRI sites of pBluescriptIISK—(manufactured by Stratagene, U.S.A.) to thereby construct plasmids (plasmids for introducing a single gene, see FIG. 2).

PPDK promoter::PEPC cDNA::NOS terminator (pDPN)
PPDK promoter::CA cDNA::35S terminator (pDCS)
PPDK promoter::PCK cDNA::35S terminator (pDKS).

Further, pDKS was digested with ClaI, blunt-ended and then digested with XbaI. The DNA fragment thus obtained was inserted into pDPN at the sites digested with SmaI and XbaI to thereby give plasmid pPK carrying the two genes, i.e., PEPC and PCK (see FIG. 2). Next, pDCS was digested with SmaI and an HindIII linker was added thereto. After being digested with HindIII, the obtained DNA fragment was inserted into the HindIII site of pDPN to thereby give plasmid pCP. Furthermore, pDKS was digested with ClaI, blunt ended and then digested with XbaI. The DNA fragment thus obtained was inserted into pCP at the site digested with SmaI and XbaI to thereby give plasmid pCPK carrying the three genes, i.e., CA, PEPC and PCK (see FIG. 2). Next, pPK was digested with XbaI and then partially digested with HindIII to thereby give a DNA fragment of about 7.5 kbp, while pCPK was digested with XbaI and then partially digested with HindIII to thereby give another DNA fragment of about 9.5 kbp. These DNA fragments were inserted into pSB11 (Komari, T. et al. Plant J. (1996)10:165–174) respectively at the sites digested with XbaI and HindIII to thereby construct superbinary intermediate plasmids pSPK and pSCPK.

These vectors were each introduced into *Escherichia coli* LE392 strain. Then introduction into Agrobacterium and homologous recombination (Komari, T. et al. Plant J. (1996) 10:165–174) were carried out via triparental mating with Agrobacterium LBA4404/pSB4 and *E. coli* HB101/pRK2013 to thereby give plasmids pSB4PK and pSB4CPK.

(7) Construction of Vectors Harboring CA, PEPC, PCK and/or PPDK

The plasmid vector pCR1000 (manufactured by Invitrogen, U.S.A.) having the PPDK promoter region, which had been obtained by the PCR method as described above, was digested with HindIII and EcoRI and then inserted between the HindIII and EcoRI sites of pBluescript IISK—(manufactured by Stratagene, U.S.A.) from which the SacI site had been deleted. Then the resultant product was digested with SacI and blunt-ended. Next, a fragment of about 200 bp containing the first intron of *Ricinus communes* catalase, (which had been obtained by digesting pIG221 (Ohta et al.:Construction and expression in tobacco of a beta-glucuronidase (GUS) reporter gene containing an intron within the coding sequence. Plant Cell Physiol. 31:805–813 (1990)) with BamHI and SalI followed by blunting,) was inserted thereinto to thereby give plasmid pSK-Di containing the PPDK (cati) promoter. This plasmid was then digested with NdeI and blunt-ended to thereby give another plasmid pSK-Di2 having the NcoI linker inserted thereinto.

cDNA of maize C4 PPDK was isolated by screening a cDNA library prepared by a conventional method (Sambrook, J. et al. ibid.) by using λZAP vector (manufactured by Stratagene, U.S.A.) with the use of the following synthetic oligonucleotide:

5'-TAGCTCGATGGGTTGCACGATCATATGGAGC AAGG-3' (SEQ ID NO: 15) prepared on the basis of the known nucleotide sequence (Matsuoka, M., Ozeki, Y., Yamamoto, N., Hirano, H., Kano-Murakami, Y. and Tanaka, Y.: Primary structure of maize pyruvate, orthophosphate dikinase as deduced from cDNA sequence, J. Biol. Chem. 163:11080–11083 (1990)). Further, the isolated maize PPDK cDNA was to achieve amplification by the PCR method (Mcpherson, M. J. et al., ibid.) with the use of the following synthetic primers prepared on the basis of the known sequence (Sheen, J.: Molecular mechanisms underlying the differential expression of Maize Pyruvate, Orthophosphate dikinase genes, Plant Cell 3:225–245 (1991)):

5'-TTTCATATGGCGCCCGTTCAATGTGCGC GTTCGCAGAGGGTGTTCCACTTCGGCAA-3' (5' side) (SEQ ID NO: 16); and 5'-GTACTCCTCCACCCACTGCA-3' (3' side) (SEQ ID NO: 17); to thereby give a DNA fragment of about 250 bp. This fragment was digested with NdeI and SacII and substituted for the region between the NdeI and SacII sites of the above-mentioned PPDK cDNA. Next, it was digested with NdeI and ClaI and the DNA fragment of about 2.9 kbp thus obtained was employed as a PPDK cDNA in the gene construction.

As the terminator region, the gene 7 terminator contained in plasmid pPGA643A (Gynheung A N, Paul R. Ebert, Amitava Mitra and Sam B. H A: binary vectors, Plant Molecular Biology Manual A3:1–19 (1988)) was used. The gene 7 terminator was obtained by digesting pPGA643 (Gynheung A N et al., ibid.) with ClaI and KpnI. The terminator was inserted between the ClaI and KpnI sites of pBluescript IISK—(manufactured by Stratagene, U.S.A.) to thereby give a plasmid. This plasmid was digested with KpnI and blunt-ended and an XbaI linker was added thereinto. After a digestion with ClaI and XbaI, the resulted DNA fragment was employed in the gene construction.

The PPDK cDNA and the gene 7 terminator were inserted between the NdeI and XbaI sites of pSK-Di to thereby give plasmid pSK-DiDT containing the PPDK gene.

A DNA fragment of about 3.4 kbp, which had been obtained by digesting the above-mentioned pDPN with XbaI and then partially digesting with NcoI, was inserted between the NcoI and XbaI sites of pSK-Di2 to thereby give a plasmid pSK-DiPN containing the PEPC gene.

A DNA fragment of about 2.4 kbp, which had been obtained by digesting the above-mentioned pDKS with NcoI and XbaI, was inserted between the NcoI and XbaI sites of pSK-Di2 to thereby give a plasmid pSK-DiKS containing the PEPCK gene.

A DNA fragment of about 1 kbp, which had been obtained by digesting the above-mentioned pDCS with NcoI and XbaI, was inserted between the NcoI and XbaI sites of pSK-Di2 to thereby give a plasmid pSK-DiCS containing the CA gene.

An SmaI linker was inserted into the Xho I site of pSK-DiPN and digested with SmaI. The DNA fragment of about 4.5 kpb thus obtained was inserted into pSK-DiCS at the site having been digested with PstI and blunt ended to thereby give a plasmid pSK-CiPi. After deleting the XbaI site of pSK-DiDT, an XbaI linker was added to the Xho I site of the plasmid, and it was digested with XbaI and Not I. The DNA fragment of about 4.8 kbp thus obtained was inserted between the XbaI and Not I sites of the plasmid pSK-CiPi to thereby give plasmid pSK-CiPiDi. An Not I linker was added to the Xho I site of pSK-CiPiDi and a digestion was effected with Not I to thereby give DNA fragment of about 12 kbp. pSB11 (Komari, T. et a 1., Plant J. 10:165–174 (1996)) was digested with HindIII and EcoRI and blunt-ended. Next, an Not I linker was added thereinto. Into this Not I site, the above-mentioned DNA fragment of about 12 kbp was inserted to thereby give plasmid pSBmCiPiDi. An XbaI linker was added to the Xho I site of pSK-DiKS and digestion was effected with XbaI. The DNA fragment of about 3.3 kbp thus obtained was inserted into the XbaI site of pSBmCiPiDi to thereby give plasmid pSBmCiPiKiDi.

Then introduction into Agrobacterium and homologous recombination (Komari, T. et al., ibid.) were carried out via triparent mating among *E. coli* DH5a strain carrying the plasmid pSBmCiPiKiDi, Agrobacterium LBA4404/carrying pSB4 and *E. coli* HB101 strain carrying pRK2013 to thereby give plasmid pSB4CiPiKiDi.

Example 2

Construction of Transformants

A Japonica rice (cultivar "Tsukinohikari") was used throughout the transformation study of rice.

Rice transformants having pDPN, pDKS and pDCS introduced thereinto were constructed by the electroporation method previously described (Japanese Patent Public Disclosure Hei 8-80197).

Rice transformants having pSB4PK, pSB4CPK and pSB4CiPiDiKi introduced thereinto were constructed by the Agrobacterium method reported described (Hiei, Y. et al. (1994) Plant J. 6:271–282).

These transformants were grown in an air-conditioned green house (daylight period: 16 hours, daytime: 28° C., nighttime: 23° C.).

Example 3

Detection of Enzyme Proteins and Measurement of Enzymatic Activities

About 0.1 g of the green leaves of the transformants or control rice ("Tsukinohikari") was homogenized in 1 ml of an ice-cold extraction buffer (50 mM HEPES-KOH pH 7.0, 10 mM magnesium chloride, 2 mM manganese chloride, 1 mM sodium pyruvate, 1 mM phosphoric acid, 1 mM EDTA, 0.1% 2-mercaptoethanol, 20% glycerol, 1 mM phenylmethylsulfonyl fluoride, 1 mM benzamidine, 1 mM 6-amino-n-caproic acid, 0.2% (w/w) isoascorbic acid, and 2% (w/v) polyclar AT). The homogenate was centrifuged at 15,000×g for 20 minutes at 4° C. Then the obtained supernatant was desalted by passing through an NAP5™ column (manufactured by Pharmacia, Sweden) which had been equilibrated at room temperature with a column buffer (50 mM HEPES-KOH pH 7.0, 10 mM magnesium chloride, 2 mM manganese chloride, 1 mM EDTA, 0.1% 2-mercaptoethanol, and 20% glycerol) to thereby give a crude extract. The chlorophyll content in the homogenate was determined by a method reported previously (Wintermans and deMots (1965) Biochem. Biophys. Acta 109:448–453), while the protein content in the crude extract was determined by using Protein Assay Kit™ (manufactured by BioRad, U.S.A.).

The expression of the enzymes in the transformants was detected by Western blotting as follows. The crude extracts obtained above were subjected to SDS-PAGE in such a manner as to adjust the protein concentration at the same level. The separated proteins in the gel were electrically transferred onto a nitrocellulose membrane (manufactured by Schleicher & Schull, Germany) and the expression of each of the proteins was detected by using a rabbit antiserum against maize PEPC protein, *Urochloa panicoides* PCK protein, spinach CA protein or maize PPDK protein, an alkaline phosphatase conjugated goat anti-rabbit IgG (manufactured by Organon Teknika, U.S.A.) and AP Immun-Blot Assay KIT™ (manufactured by BioRad, U.S.A.).

The PEPC activity was determined by measuring the decreasing rate of the absorption of NADH at 340 nm with the use of 1 ml of a reaction mixture containing 25 mM HEPES-KOH (pH 8.0), 5 mM magnesium sulfate, 4 mM dithiothreitol, 5 mM potassium hydrogencarbonate, 0.25 mM NADH, 1 mM glucose-6-phosphate, 5 mM phosphoenolpyruvate, 1 U malate dehydrogenase (manufactured by Boehringer Mannheim, Germany) and 25 $\mu$l of the crude extract.

The PCK activity was determined by measuring the decreasing rate of the absorption of oxaloacetic acid at 280 nm with the use of 1 ml of a reaction mixture containing 25 mM HEPES-KOH (pH 8.0), 4 mM dithiothreitol, 0.2 mM oxaloacetic acid, 1 U pyruvate kinase (manufactured by Boehringer Mannheim, Germany), 0.2 mM ATP and 50 $\mu$l of the crude extract.

The CA activity was determined by adding 0.5 ml of an ice-cold, carbon dioxide saturated water to 0.3 ml of a 50 mM HEPES-KOH buffer (pH 8.0) stained with Bromothymol Blue and 10 $\mu$l of the crude extract and measuring the time required until the coloration of the reaction mixture disappeared on ice. The activity was calculated in accordance with the method reported previously (Burnell, J. N. and Hatch, M. D. (1988) Plant Physiol. 86:1252–1256).

The PPDK activity was determined by measuring the decreasing rate of the absorption of NADH at 340 nm with the use of 1 ml of a reaction mixture containing 25 mM HEPES-KOH (pH 8.0), 10 mM dithiothreitol, 10 mM potassium hydrogencarbonate, 8 mM magnesium sulfate, 5 mM ammonium chloride, 2.5 mM monosodium hydrogenphosphate, 1 mM ATP, 1 mM of glucose-6-phosphate, 5 mM of sodium pyruvate, 0.2 mM NADH, 2 U malate dehydrogenase, 2 U PEPC (manufactured by Wako Pure Chemical Industries, Japan) and 200 $\mu$l of the crude extract.

Example 4

Tracer Experiment with $^{14}CO_2$

Leaf tips (about 5 cm) of the rice transformant and the control ("Tsukinohikari"), which had been grown in an air-conditioned green house, were detached and each cut end was covered with absorbent cotton immersed in water. These samples were set in an assimilation chamber (about 120 ml or 50 ml in capacity) made by the inventors. After passing the open air at a flow rate of about 5 l/min for 30 minutes under irradiation at about 27,000 lx, radioactive carbon dioxide gas, which had been generated by mixing 100–180 $\mu$l of 60% perchloric acid with a 50–70 $\mu$Ci NaH$^{14}$CO$_3$ solution (manufactured by Amersham, England) in a gas-tight syringe, was injected into the closed system. After a pulse of 5 seconds, the leaves were frozen in liquid nitrogen to cease any biological activities and then put in 80% hot ethanol for about 30 minutes to thereby extract soluble matters. After a pulse of 5 seconds, the open air was introduced into the system. 10, 30 and 90 seconds thereafter, the leaf samples were taken out from the chamber and immersed in liquid nitrogen to cease any biological activities. Then soluble matters were extracted in 80% hot ethanol. The extracts thus obtained were each evaporated on an evaporator and subjected to two-dimensional thin layer chromatography on Funaseru SF Cellulose Thin Layer Plate™ (manufactured by Funakoshi Japan, 20 cm×20 cm).

The development was effected at room temperature by using a mixture of phenol-water-glacial acetic acid-0.5 M EDTA (47:84:5.5:1.14, v/v) as the primary developing solvent and an isovolumetric mixture of a solution A (n-butanol:water, 74:5, v/v) with a solution B (propionic acid:water, 9:11, v/v) as the secondary developing solvent. After the completion of the development, the plate was dried followed by autoradiography with Bioimage Analyzer Bas 1000 System (Fuji Film Japan) to determinate the relative amount of each spot. Thus the proportion of the substance labeled with the radioisotope was examined.

Example 5

Tracer Experiment with [$^{14}$C] malate

Leaves of the rice transformant and the control ("Tsukinohikari"), which had been grown in an air-conditioned green house, were detached, put into a 10 mM phosphate buffer (pH 6.4) and then irradiated at 27,000 lx for 1 hour. Next, these leaves were put into a 100 μl of the solution to which 5 μl of 1 μCi [$^{14}$C] malate (manufactured by Amersham, England) had been added. After a determined period of time, the leaf samples were taken out. Then the part immersed in the solution was removed and immersed in boiling 80% ethanol to thereby cease any biological activities. Soluble matters were allowed to elute therefrom by boiling for 30 minutes. The elute was evaporated on an evaporator. The substance labeled with the radioisotope was separated by two-dimensional thin layer chromatography followed by autoradiography with Bioimage Analyzer Bas 1000 System to determine the radioactivity of each spot. Thus the relative amount of the substance labeled with the radioisotope was examined.

Example 6

Measurement of photosynthetic Activity

Rice transformants having three genes introduced thereinto and the control ("Tsukinohikari"), which had been grown in the air-conditioned green house, were transferred to be grown in a growth cabinet (daylight period: 12 hours, illumination: about 35,000 lx, 25° C.) for acclimatization. Then the photosynthetic activities of fully expanded leaves showing no symptom of senescence were measured with a photosynthesis measurement system (LI-6200, manufactured by LI-COR, U.S.A.).

Example 7

Production of Transgenic Rice with PCK Type C4 Pathway and Determination Data

Transformant individuals were made for each gene construct prepared above and the expression of the transgenes were examined by Western blotting. Among 19 rice transformants having the gene construct PDPN introduced thereinto (transformant with PEPC), the expression of PEPC protein was confirmed in 15 transformants. Among 31 rice transformants having the gene construct pDKS introduced thereinto (transformant with PCK), the expression of PCK protein was confirmed in 20 transformants. Among 41 rice transformants having the gene construct pDCS introduced thereinto (transformant with CA), the expression of CA protein at relatively high levels was confirmed in 3 transformants. Among 21 rice transformants having the gene construct pSB4PK introduced thereinto (transformant with two genes), the expression of two proteins, i.e., PEPC and PCK, was confirmed in 12 transformants. Among 40 rice transformants having the gene construct pSB4CPK introduced thereinto (transformant with three genes), the expression of three proteins, i.e., CA, PEPC and PCK, was confirmed in 15 transformants. Among 72 rice transformants having the gene construct pSB4CiPiKiDi introduced thereinto (transformant with four genes), the expression of four proteins, i.e., CA, PEPC, PCK and PPDK, was confirmed in 22 transformants.

R1 progenies were made from, among these rice transformants, showing relatively high expression levels of the enzymes introduced thereinto. Then the activity of each enzyme in crude extracts of green leaves was examined. Table 1 shows the results. As Table 1 clearly shows, the crude extracts of the R1 generation transformants showed higher activities of the enzymes introduced thereinto than those in the control rice ("Tsukinohikari"). These facts indicate that the enzymes expressed from the introduced genes in the transformants exhibit their enzymatic activities. The gene constructs for PCK introduction employed in this Example were chimera genes to which the region encoding the transit peptide of rice Rubisco small subunit had been added, similar to those reported previously (Japanese Patent Public Disclosure Hei 8-80197). Thus, the PCK protein can be localized in chloroplasts due to the action of the transit peptide.

TABLE 1

Activity of enzymes in rice transformants

| | Enzymatic activity (U/mg chlorophyll) | | | |
|---|---|---|---|---|
| | CA | PEPC | PCK | PPDK |
| transformant with CA | 18,760 | 0.458 | 0 | nd |
| transformant with PEPC | 2,250 | 1.880 | 0 | nd |
| transformant with PCK | 1,364 | 0.474 | 7.744 | nd |
| transformant with 2 genes | 2,143 | 1.171 | 5.780 | nd |
| transformant with 3 genes | 9,269 | 1.071 | 3.001 | nd |
| transformant with 4 genes | 9,450 | 1.490 | 3.170 | 0.37 |
| control (Tsukinohikari) | 2,171 | 0.322 | 0 | 0.29 | nd: not determined.

$^{14}CO_2$ was supplied to leaf sections of the plants of the R1 generation of the rice transformants having two and three genes introduced thereinto and the control (Tsukinohikari). After 5 seconds, biological activities in the tissues were ceased and the relative amount of the labeled C4 compounds was examined. As a result, it was found that the contents of labeled malate and labeled aspartic acid in the transformants were respectively about 10 times and about 2 times higher than those in the control sample (see Table 2). These facts indicate that the introduced PEPC functioned in the green leaf tissues of the transformants so that the first carbon dioxide fixation process in the C4 photosynthetic pathway was performed therein.

TABLE 2

Tracer experiment with $^{14}CO_2$

| | $^{14}C$ uptake (%) | |
|---|---|---|
| | malate | aspartate |
| (Tsukinohikari) | 0.7 | 0.9 |
| transformant with 2 genes | 9.8 | 2.0 |
| transformant with 3 genes | 8.1 | 1.9 |

Figure 3:
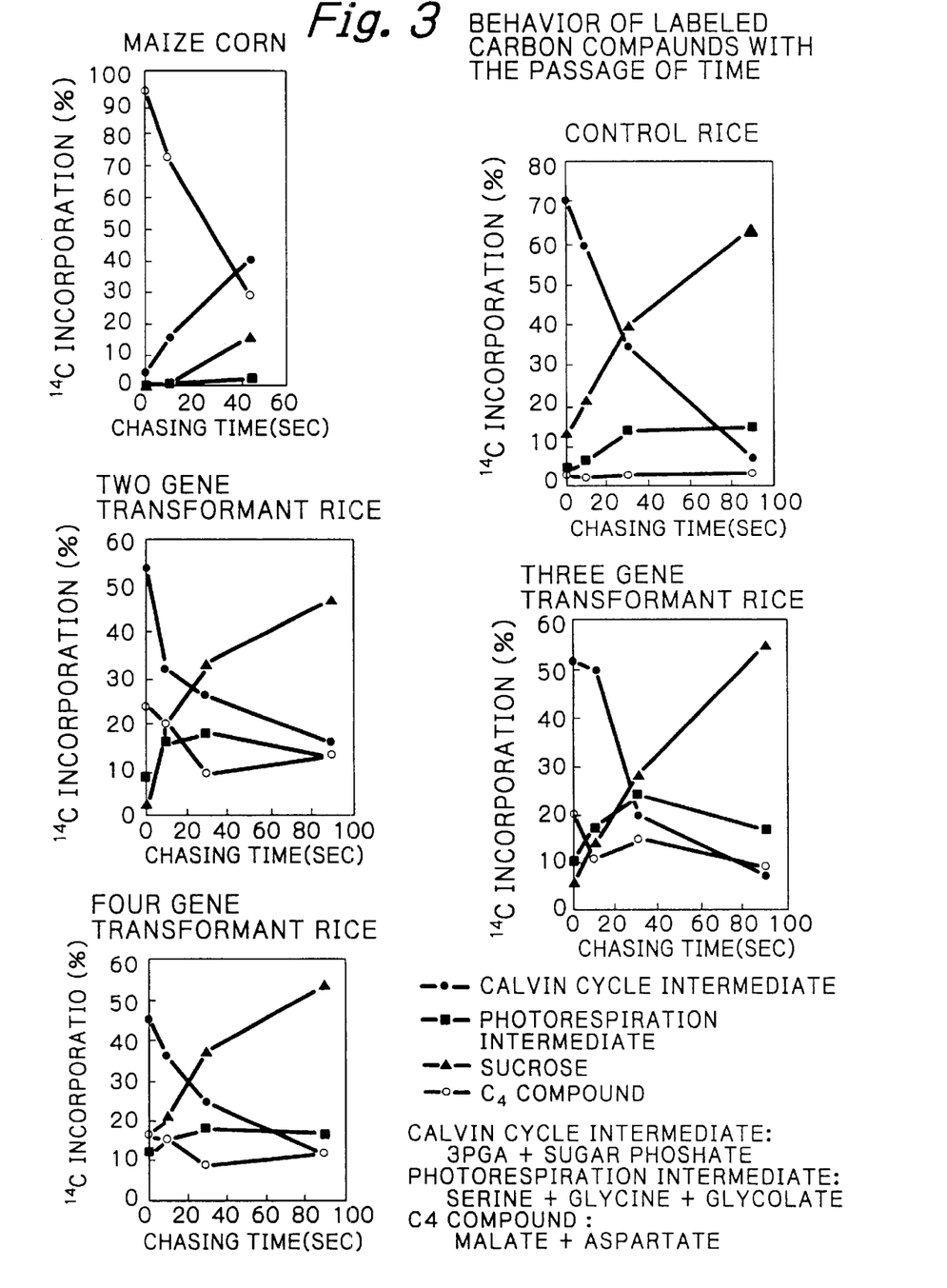
FIG. 3 is a graph wherein the relative amount of isotope-labeled carbon compound is plotted against the course of time.

Also, $^{14}CO_2$ was supplied for 5 seconds to leaf sections of R1 generations of the rice transformants having two, three or four genes introduced thereinto, as well as the rice control (Tsukinohikari) and maize control. Subsequently, the behavior of the labeled C4 compounds was chased with the passage of time. In the rice transformants, the labeled C4 compounds decreased similar to the case of maize (i.e., a C4 plant). In contrast thereto, the labeled C4 compounds in the rice control did not show any significant change (see FIG. 3). These facts indicate that, in the rice transformants, the C4 compounds formed by the carbon dioxide fixation by the introduced PEPC were immediately metabolized into other substances, similar to the phenomena observed in green leaf tissues of C4 plants.

[$^{14}$C] malate was supplied to leaf sections of the R1 progenies of the rice transformants having two and three genes introduced thereinto and the control (Tsukinohikari). After 15 minutes, biological activities in the tissues were ceased and the proportion of the labeled compounds were examined. As a result, it was found that the relative amount of labeled sucrose in the transformants were about 3 times higher than that in the control sample (see Table 3). This fact indicates that the introduced PCK functioned in the green leaf tissues of the rice transformants so that carbon dioxide was passed from the C4 compound in the C4 photosynthetic pathway to the Calvin-Benson cycle.

TABLE 3

Tracer experiment with [$^{14}$C] malate

| | $^{14}$C uptake into sucrose (%) |
|---|---|
| control (Tsukinohikari) | 6.2 |
| transformant with 2 genes | 15.7 |
| transformant with 3 genes | 22.5 |

Figure 4:
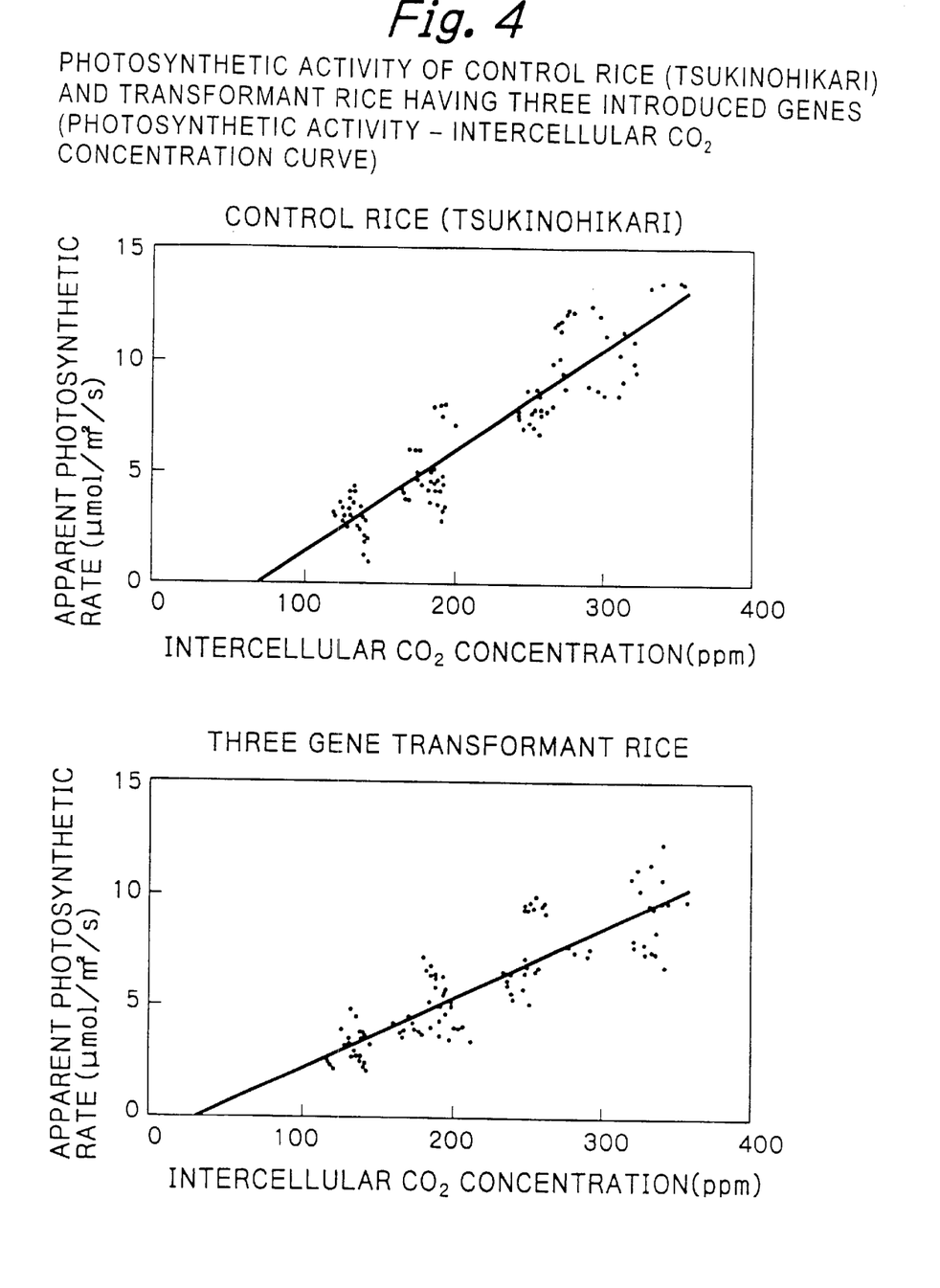
FIG. 4 is a graph showing the photosynthetic activity of the transformed rice.

The photosynthetic activities of R1 progenies of the rice transformant having 3 genes introduced thereinto and the rice control (Tsuki no Hikari) were measured while varying the concentration of carbon dioxide supplied to the leaves. The rate of photosynthesis was plotted against intercellular carbon dioxide concentration (see FIG. 4). As a result, the intercellular carbon dioxide concentration of the transformant at the point that the apparent photosynthetic activity was assumed to disappear (i.e., the intercept on the axis x of the line in FIG. 4) was lower than that of the rice control. This fact means that the $CO_2$ compensation point of the rice transformant is lower than that of the control. In general, C4 plants show $CO_2$ compensation points lower than those of C3 plants. Thus, it can be concluded that the rice transformants constructed herein are similar in photosynthetic characteristics to C4 plants as compared with the rice control.

The results described above indicate that the rice transformants having two and three genes introduced thereinto contain active forms of the enzymes relating to C4 photosynthesis, which are the expression products of the introduced genes, and, moreover, that the C4 photosynthetic pathway functions in these plants so as to enhance the photosynthetic potency. Accordingly, the present invention enables the PCK type C4 photosynthetic pathway to function in C3 plant cells to thereby alter the photosynthetic potency.

EFFECTS OF THE INVENTION

According to the present invention, a cyclic reaction similar to the C4 photosynthetic pathway of C4 plants can be actuated in mesophyll cells of C3 plants so as to impart the C3 plants a function of elevating the carbon dioxide concentration in chloroplasts and another function of avoiding photoinhibition due to ATP consumption. Because of the enhanced photosynthetic potency, plants acquired these functions are expected to achieve elevated yield per dry weight, improved drought resistance, improved high temperature resistance, improved tolerance to high light intensity and enhanced photosynthetic potency under low carbon dioxide conditions.

What is claimed is:

1. A method for transforming a rice plant to provide the plant with a photosynthetic pathway formed in a single cell to mimic the C4 photosynthetic pathway which comprises introducing into a rice plant a gene coding for a phosphoenolpyruvate carboxylase (PEPC), wherein the PEPC gene is operably linked to a promoter; and a gene coding for a phosphoenolpyruvate carboxykinase (PKC), wherein the PCK gene is operably linked to a promoter and a gene coding for a chloroplast transit peptide.

2. The method according to claim 1 which further comprises introducing a gene coding for a carbonic anhydrase (CA) into the rice plant, wherein the CA gene is operably linked to a promoter.

3. The method according to claim 1 which further comprises introducing a gene coding for a pyruvate, orthophosphate dikinase (PPDK) into the rice plant, wherein the PPDK gene is operably linked to a promoter.

4. The method according to claim 2 which further comprises introducing a gene coding for a pyruvate, orthophosphate dikinase (PPDK) into the rice plant, wherein the PPDK gene is operably linked to a promoter.

5. The method according to any one of claims 1–3 and 4 wherein the promoter operably linked to each of the genes is a photosynthetic tissue specific promoter.

6. The method according to claim 5 wherein two or more or all of said genes are carried on a single gene construct.

7. A chimeric gene comprising a gene coding for a phospoenolpyruvate carboxylase (PEPC), and a gene coding for a phosphoenolpyruvate carboxykinase (PCK) which has been operably linked to a DNA fragment coding for a transit peptide.

8. A transformed rice plant comprising a gene coding for a phospoenolpyruvate carboxylase (PEPC), and a gene coding for a phosphoenolpyruvate carboxykinase (PCK), wherein the PEPC gene is operably linked to a promoter, and the PCK gene is operably linked to a promoter and a gene coding for a chloroplast transit peptide.

9. The transformed rice plant as claimed in claim 8 wherein the PEPC and PCK enzymes form a photosynthetic pathway in a single cell to mimic the photosynthetic pathway of a C4 plant, in concert with a gene coding for a carbonic anhydrase (CA) and a gene coding for a pyruvate, orthophosphate dikinase (PPDK).

10. The transformed rice plant according to claim 9 wherein each of the PEPC gene and the PCK gene is operably linked to a promoter specific to a photosynthetic tissue.

11. The transformed rice plant according to claim 9 or 10 wherein one or both of the CA gene and the PPDK gene are endogenous to the rice plant.

12. The transformed rice plant according to claim 9 or 10 wherein one or both of the CA gene and the PPDK gene are isolated from another plant and operably linked to a promoter specific to a photosynthetic tissue.

* * * * *

SEQUENCE LISTING

```
<160> NUMBER OF SEQ ID NOS: 17

<210> SEQ ID NO 1
<211> LENGTH: 930
<212> TYPE: DNA
<213> ORGANISM: Zea mays - Inbred B73
<220> FEATURE:
<221> NAME/KEY: misc_feature
<222> LOCATION: ()..()
<223> OTHER INFORMATION: C4 type PPDK gene promoter region (partial)

<400> SEQUENCE: 1
ctaaagacat ggaggtggaa ggcctgacgt agatagagaa gatgctctta gctttcattg      60
tctttctttt gtagtcatct gatttacctc tctcgtttat acaactggtt tttaaacac      120 tccttaactt ttcaaattgt ctctttcttt acccactagact agataatttt aatggtgatt     180
ttgctaatgt ggcgccatgt tagatagagg taaaatgaac tagttaaaag ctcagagtga      240
taaatcaggc tctcaaaaat tcataaactg tttttttaaat atccaaatat ttttacatgg     300
aaaataataa aatttagttt agtattaaaa aattcagttg aatatagttt tgtcttcaaa     360
aattatgaaa ctgatcttaa ttatttttcc ttaaaaccgt gctctatctt tgatgtctag     420
tttgagacga ttatataatt tttttttgtgc ttactacgac gagctgaagt acgtagaaat   480
actagtggag tcgtgccgcg tgtgcctgta gccactcgta cgctacagcc caagcgctag     540
agcccaagag gccggagtgg aaggcgtcgc ggcactatag ccactcgccg caagagccca     600
```

```
agagaccgga gctggaagga tgagggtctg ggtgttcacg aattgcctgg aggcaggagg      660
ctcgtcgtcc ggagcacagg cgtggagaac gtccgggata aggtgagcag ccgctgcgat      720
aggcgcgtgt gaaccccgtc gcgccccacg gatggtataa gaataaaggc attccgcgtg      780
caggattcac ccgttcgcct ctcacctttt cgctgtactc actcgccaca cacacccct       840 ctccagctcc gttggagctc cggacagcag caggcgcggg gcggtcacgt agtaagcagc      900
tctcggctcc ctctcccctt gctccatatg                                       930
```

```
<210> SEQ ID NO 2
<211> LENGTH: 153
<212> TYPE: DNA
<213> ORGANISM: Oryza sativa - Nihonbare
<220> FEATURE:
<221> NAME/KEY: CDS
<222> LOCATION: (1)..(153)
<221> NAME/KEY: misc_feature
<222> LOCATION: ()..()
<223> OTHER INFORMATION: Transit sequence region of RUBISCO small
      subunit

<400> SEQUENCE: 2 atg gcc ccc tcc gtg atg gcg tcg tcg gcc acc acc gtc gct ccc ttc       48
Met Ala Pro Ser Val Met Ala Ser Ser Ala Thr Thr Val Ala Pro Phe
1               5                  10                  15 cag ggg ctc aag tcc acc gcc ggc atg ccc gtc gcc cgc cgc tcc ggc       96
Gln Gly Leu Lys Ser Thr Ala Gly Met Pro Val Ala Arg Arg Ser Gly
            20                  25                  30 aac tcc agc ttc ggc aac gtc agc aat ggc ggc agg atc agg tgc atg      144
Asn Ser Ser Phe Gly Asn Val Ser Asn Gly Gly Arg Ile Arg Cys Met
        35                  40                  45 cag tct aga                                                          153
Gln Ser Arg
    50
```

```
<210> SEQ ID NO 3
<211> LENGTH: 51
<212> TYPE: PRT
<213> ORGANISM: Oryza sativa - Nihonbare
<220> FEATURE:
<221> NAME/KEY: misc_feature
<222> LOCATION: ()..()
<223> OTHER INFORMATION: Transit sequence region of RUBISCO small
      subunit

<400> SEQUENCE: 3

Met Ala Pro Ser Val Met Ala Ser Ser Ala Thr Thr Val Ala Pro Phe
1               5                  10                  15

Gln Gly Leu Lys Ser Thr Ala Gly Met Pro Val Ala Arg Arg Ser Gly
            20                  25                  30

Asn Ser Ser Phe Gly Asn Val Ser Asn Gly Gly Arg Ile Arg Cys Met
        35                  40                  45

Gln Ser Arg
    50
```

```
<210> SEQ ID NO 4
<211> LENGTH: 697
<212> TYPE: DNA
<213> ORGANISM: Spinacia oleracea
<220> FEATURE:
<221> NAME/KEY: CDS
<222> LOCATION: (3)..(668)
<221> NAME/KEY: misc_feature
<222> LOCATION: ()..()
```

<223> OTHER INFORMATION: carbonic anhydrase without transit peptide coding region.

<400> SEQUENCE: 4

```
cc atg gag tta gcc gac ggt ggc aca cca tcc gcc agt tac ccg gtt       47
   Met Glu Leu Ala Asp Gly Gly Thr Pro Ser Ala Ser Tyr Pro Val
   1               5                  10                  15 cag aga att aag gaa ggg ttt atc aaa ttc aag aag gag aaa tac gag      95
Gln Arg Ile Lys Glu Gly Phe Ile Lys Phe Lys Lys Glu Lys Tyr Glu
                20                  25                  30 aaa aat cca gca ttg tat ggt gag ctt tct aag ggc caa gct ccc aag     143
Lys Asn Pro Ala Leu Tyr Gly Glu Leu Ser Lys Gly Gln Ala Pro Lys
                    35                  40                  45 ttt atg gtg ttt gcg tgc tca gac tcc cgt gtg tgt ccc tcg cac gta     191
Phe Met Val Phe Ala Cys Ser Asp Ser Arg Val Cys Pro Ser His Val
                50                  55                  60 cta gat ttc cag ccc ggt gag gct ttc atg gtt cgc aac atc gcc aac     239
Leu Asp Phe Gln Pro Gly Glu Ala Phe Met Val Arg Asn Ile Ala Asn
65                  70                  75 atg gtg cca gtg ttt gac aag gac aaa tac gct gga gtc gga gca gcc     287
Met Val Pro Val Phe Asp Lys Asp Lys Tyr Ala Gly Val Gly Ala Ala
80                  85                  90                  95 att gaa tac gca gtg ttg cac ctt aag gtg gag aac att gtc gtg att     335
Ile Glu Tyr Ala Val Leu His Leu Lys Val Glu Asn Ile Val Val Ile
                100                 105                 110 gga cac agt gct tgt ggt gga atc aag ggg ctt atg tct tct cca gat     383
Gly His Ser Ala Cys Gly Gly Ile Lys Gly Leu Met Ser Ser Pro Asp
                    115                 120                 125 gca gga cca acc aca act gat ttt att gag gat tgg gtc aaa atc tgc     431
Ala Gly Pro Thr Thr Thr Asp Phe Ile Glu Asp Trp Val Lys Ile Cys
                130                 135                 140 ttg cct gcc aag cac aag gtg tta gcc gag cat ggt aat gca act ttc     479
Leu Pro Ala Lys His Lys Val Leu Ala Glu His Gly Asn Ala Thr Phe
145                 150                 155 gct gaa caa tgc acc cat tgt gaa aag gaa gct gtg aat gta tct ctt     527
Ala Glu Gln Cys Thr His Cys Glu Lys Glu Ala Val Asn Val Ser Leu
160                 165                 170                 175 gga aac ttg ttg act tac cca ttt gta aga gat ggt ttg gtg aag aag     575
Gly Asn Leu Leu Thr Tyr Pro Phe Val Arg Asp Gly Leu Val Lys Lys
                180                 185                 190 act cta gct ttg cag ggt ggt tac tac gat ttt gtc aat gga tca ttc     623
Thr Leu Ala Leu Gln Gly Gly Tyr Tyr Asp Phe Val Asn Gly Ser Phe
                    195                 200                 205 gag cta tgg gga ctc gaa ttc ggc ctc tct cct tcc caa tct gta         668
Glu Leu Trp Gly Leu Glu Phe Gly Leu Ser Pro Ser Gln Ser Val
                210                 215                 220 tgaaccaaca caaccatttg actgcatgc                                     697
```

<210> SEQ ID NO 5
<211> LENGTH: 222
<212> TYPE: PRT
<213> ORGANISM: Spinacia oleracea
<220> FEATURE:
<221> NAME/KEY: misc_feature
<222> LOCATION: ()..()
<223> OTHER INFORMATION: carbonic anhydrase without transit peptide coding region.

<400> SEQUENCE: 5

```
Met Glu Leu Ala Asp Gly Gly Thr Pro Ser Ala Ser Tyr Pro Val Gln
1               5                   10                  15
```

```
Arg Ile Lys Glu Gly Phe Ile Lys Phe Lys Glu Lys Tyr Glu Lys
            20                  25                  30

Asn Pro Ala Leu Tyr Gly Glu Leu Ser Lys Gly Gln Ala Pro Lys Phe
         35                  40                  45

Met Val Phe Ala Cys Ser Asp Ser Arg Val Cys Pro Ser His Val Leu
 50                  55                  60

Asp Phe Gln Pro Gly Glu Ala Phe Met Val Arg Asn Ile Ala Asn Met
 65                  70                  75                  80

Val Pro Val Phe Asp Lys Asp Lys Tyr Ala Gly Val Gly Ala Ala Ile
                 85                  90                  95

Glu Tyr Ala Val Leu His Leu Lys Val Glu Asn Ile Val Ile Gly
             100                 105                 110

His Ser Ala Cys Gly Gly Ile Lys Gly Leu Met Ser Ser Pro Asp Ala
             115                 120                 125

Gly Pro Thr Thr Thr Asp Phe Ile Glu Asp Trp Val Lys Ile Cys Leu
            130                 135                 140

Pro Ala Lys His Lys Val Leu Ala Glu His Gly Asn Ala Thr Phe Ala
145                 150                 155                 160

Glu Gln Cys Thr His Cys Glu Lys Glu Ala Val Asn Val Ser Leu Gly
                165                 170                 175

Asn Leu Leu Thr Tyr Pro Phe Val Arg Asp Gly Leu Val Lys Lys Thr
            180                 185                 190

Leu Ala Leu Gln Gly Tyr Tyr Asp Phe Val Asn Gly Ser Phe Glu
            195                 200                 205

Leu Trp Gly Leu Glu Phe Gly Leu Ser Pro Ser Gln Ser Val
            210                 215                 220

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer derived from maize

<400> SEQUENCE: 6
ctaaagacat ggaggtggaa g                                         21

<210> SEQ ID NO 7
<211> LENGTH: 19
<212> TYPE: DNA
<213> ORGANISM: Artificial Sequence
<220> FEATURE:
<223> OTHER INFORMATION: Synthetic Primer derived from maize

<400> SEQUENCE: 7
gtagctcgat gggtgcacg                                            19

<210> SEQ ID NO 8
<211> LENGTH: 35
<212> TYPE: DNA
<213> ORGANISM: Artificial Sequence
<220> FEATURE:
<223> OTHER INFORMATION: Synthetic DNA Probe

<400> SEQUENCE: 8
gccatggcgc ggcgggaagc taagcacgga agcga                          35

<210> SEQ ID NO 9
<211> LENGTH: 39
<212> TYPE: DNA
```

<213> ORGANISM: Artificial Sequence
<220> FEATURE:
<223> OTHER INFORMATION: Synthetic PCR primer

<400> SEQUENCE: 9
gctctagatc tctggcacgt gaatatggcc ccaacctcg                     39

<210> SEQ ID NO 10
<211> LENGTH: 39
<212> TYPE: DNA
<213> ORGANISM: Artificial Sequence
<220> FEATURE:
<223> OTHER INFORMATION: Synthetic PCR primer

<400> SEQUENCE: 10
cagtgcatgc cgccgaacag gcatacagat ttacaccag                     39

<210> SEQ ID NO 11
<211> LENGTH: 29
<212> TYPE: DNA
<213> ORGANISM: Artificial Sequence
<220> FEATURE:
<223> OTHER INFORMATION: Synthetic DNA primer derived from rice Rubisco
      small subunit

<400> SEQUENCE: 11
ggaattccat ggtgcatctc aagaagtac                                29

<210> SEQ ID NO 12
<211> LENGTH: 25
<212> TYPE: DNA
<213> ORGANISM: Artificial Sequence
<220> FEATURE:
<223> OTHER INFORMATION: Synthetic DNA primer derived from rice Rubisco
      small subunit

<400> SEQUENCE: 12
gctctagact gcatgcacct gatcc                                    25

<210> SEQ ID NO 13
<211> LENGTH: 27
<212> TYPE: DNA
<213> ORGANISM: Artificial Sequence
<220> FEATURE:
<223> OTHER INFORMATION: Synthetic DNA primer derived from rice Rubisco
      small subunit

<400> SEQUENCE: 13
ggaattccat ggccccctcc gtgatgg                                  27

<210> SEQ ID NO 14
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 14
ggtggcacag ataaccatgg atccagttag ccgacggtgg c                  41

<210> SEQ ID NO 15
<211> LENGTH: 35
<212> TYPE: DNA
<213> ORGANISM: Artificial Sequence
<220> FEATURE:
<223> OTHER INFORMATION: Synthetic Primer derived from maize

```
<400> SEQUENCE: 15
tagctcgatg ggttgcacga tcatatggag caagg                              35

<210> SEQ ID NO 16
<211> LENGTH: 56
<212> TYPE: DNA
<213> ORGANISM: Artificial Sequence
<220> FEATURE:
<223> OTHER INFORMATION: Synthetic Primer derived from maize

<400> SEQUENCE: 16
tttcatatgg cgcccgttca atgtgcgcgt tcgcagaggg tgttccactt cggcaa       56

<210> SEQ ID NO 17
<211> LENGTH: 20
<212> TYPE: DNA
<213> ORGANISM: Artificial Sequence
<220> FEATURE:
<223> OTHER INFORMATION: Synthetic Primer derived from maize

<400> SEQUENCE: 17
gtactcctcc acccactgca                                               20
```